US012642485B2

(12) United States Patent
Schnall

(10) Patent No.: US 12,642,485 B2
(45) Date of Patent: Jun. 2, 2026

(54) METHOD AND APPARATUS FOR NON-INVASIVE DETECTION OF PHYSIOLOGICAL AND PATHO-PHYSIOLOGICAL SLEEP CONDITIONS

(71) Applicant: ITAMAR MEDICAL LTD., Ceasarea (IL)

(72) Inventor: Robert P. Schnall, Kiryat Bialik (IL)

(73) Assignee: ZOLL Medical Corporation, Chelmsford, MA (US)

( * ) Notice: Subject to any disclaimer, the term of this patent is extended or adjusted under 35 U.S.C. 154(b) by 1049 days.

(21) Appl. No.: 17/509,226

(22) Filed: Oct. 25, 2021

(65) Prior Publication Data

US 2022/0211323 A1 Jul. 7, 2022

Related U.S. Application Data

(63) Continuation of application No. 16/207,520, filed on Dec. 3, 2018, now abandoned, which is a continuation
(Continued)

(51) Int. Cl.
*A61B 5/00* (2006.01)
*A61B 5/02* (2006.01)
(Continued)

(52) U.S. Cl.
CPC .............. *A61B 5/4818* (2013.01); *A61B 5/02* (2013.01); *A61B 5/02028* (2013.01);
(Continued)

(58) Field of Classification Search
None
See application file for complete search history.

(56) References Cited

U.S. PATENT DOCUMENTS 5,178,151 A * 1/1993 Sackner ............... A61B 5/1135
600/526
5,398,682 A 3/1995 Lynn .................. A61B 5/14551
128/204.18
(Continued)

FOREIGN PATENT DOCUMENTS

CN 101035584 A 9/2007
JP H11309120 11/1999

OTHER PUBLICATIONS

Search Report—Corresponding PCT Application No. PCT/IB2017/053154, dated Aug. 20, 2017, 7 pages.
(Continued)

*Primary Examiner* — Michael R Bloch
(74) *Attorney, Agent, or Firm* — The Webb Law Firm

(57) ABSTRACT

Method and apparatus for the non-invasive detection of certain breathing conditions, certain sleep disordered breathing conditions, or assessment of the person's myocardial contractility and its dynamic changes, comprising steps of: determining the sleep or wake status of a person, monitoring circulatory pulse waveforms and amplitude normalized pulse wave systolic upstrokes recorded from a person's body and determining at least one index of the upstroke to characterize the strength of the contraction of the heart during the systolic upstroke during a series of heart beats relating to a breathing cycle or an absent anticipated breathing cycle of the patient, and determining that a certain change in a breathing condition, a sleep disordered breathing condition, or assessment of the person's myocardial contractility and its dynamic changes, has occurred when a specific change in the sleep disordered breathing analysis, and the at least one index of the upstroke has been detected.

14 Claims, 8 Drawing Sheets

Related U.S. Application Data of application No. PCT/IB2017/053154, filed on May 29, 2017.

(60) Provisional application No. 62/347,111, filed on Jun. 8, 2016.

(51) Int. Cl.

| | |
|---|---|
| *A61B 5/0205* | (2006.01) |
| *A61B 5/024* | (2006.01) |
| *A61B 5/08* | (2006.01) |
| *A61B 5/0245* | (2006.01) |
| *A61B 5/1455* | (2006.01) |
| *A61B 8/00* | (2006.01) |
| *A61B 8/02* | (2006.01) |

(52) U.S. Cl.

CPC ........ *A61B 5/0205* (2013.01); *A61B 5/02055* (2013.01); *A61B 5/024* (2013.01); *A61B 5/0816* (2013.01); *A61B 5/4812* (2013.01); *A61B 5/7235* (2013.01); *A61B 5/7275* (2013.01); *A61B 5/7278* (2013.01); *A61B 5/02416* (2013.01); *A61B 5/02444* (2013.01); *A61B 5/0245* (2013.01); *A61B 5/0826* (2013.01); *A61B 5/14551* (2013.01); *A61B 8/02* (2013.01); *A61B 8/488* (2013.01)

(56) References Cited

U.S. PATENT DOCUMENTS

| | | | | |
|---|---|---|---|---|
| 6,129,675 | A * | 10/2000 | Jay | A61B 5/0205 |
| | | | | 600/323 |
| 6,223,064 | B1 | 4/2001 | Lynn | |
| 6,616,613 | B1 | 9/2003 | Goodman | |
| 7,690,378 | B1 | 4/2010 | Turcott | A61B 5/0816 |
| | | | | 128/204.23 |
| 2002/0029000 | A1 | 3/2002 | Ohsaki et al. | |
| 2003/0000522 | A1 | 1/2003 | Lynn et al. | |
| 2003/0158466 | A1 | 8/2003 | Lynn | G16H 50/70 |
| | | | | 600/300 |
| 2004/0059236 | A1 | 3/2004 | Margulies | |
| 2005/0085865 | A1 | 4/2005 | Tehrani | |
| 2005/0217674 | A1 * | 10/2005 | Burton | A61B 5/08 |
| | | | | 128/204.23 |
| 2006/0189872 | A1 | 8/2006 | Arnold | A61B 5/0205 |
| | | | | 600/483 |
| 2008/0066753 | A1 | 3/2008 | Martin et al. | |
| 2008/0190430 | A1 | 8/2008 | Melker | A61B 5/4884 |
| | | | | 128/204.23 |
| 2010/0016694 | A1 | 1/2010 | Martin | A61M 16/0051 |
| | | | | 600/324 |
| 2012/0125337 | A1 * | 5/2012 | Asanoi | A61M 16/026 |
| | | | | 128/204.23 |
| 2013/0006121 | A1 | 1/2013 | Myers | |
| 2014/0128697 | A1 | 5/2014 | Parfenova et al. | |

OTHER PUBLICATIONS

Search Report—Corresponding European Application No. 17809808, dated Jan. 23, 2020, 8 pages.

Goff, Elizabeth A. et al., "The Cardiovascular Response to Arousal from Sleep Decreases with Age in Healthy Adults", Sleep, vol. 31, No. 7, 2008, pp. 1009-1017.

Bonnet, Michael H. et al., "EEG Arousal Norms by Age", Journal of Clinical Sleep Medicine, vol. 3, No. 3, 2007, pp. 271-274.

Lavie, Peretz, et al., "Peripheral Arterial Tonometry: A Novel and Sensitive Non-Invasive Monitor of Brief Arousals During Sleep", IMAJ, vol. 2, Mar. 2000, pp. 246-247.

O'Donnell, Christopher P. et al., "The Effect of Upper Airway Obstruction and Arousal on Peripheral Arterial Tonometry in Obstructive Sleep Apnea", Am. J Respir. Crit. Care Med., vol. 166, 2002, pp. 965-971.

Pillar Giora, et al., "Autonomic Arousal Index: an Automated Detection Based on Peripheral Arterial Tonometry", Sleep, vol. 25, No. 5, 2002, pp. 541-547.

Schnall Robert P. et al., "Periodic, Profound Peripheral Vasoconstriction—A New Marker of Obstructive Sleep Apnea", Sleep, vol. 22, No. 7, 1999, pp. 939-946.

Tauman, Riva et al., "Peripheral Arterial Tonometry Events and Electroencephalographic Arousals in Children", Sleep, vol. 27, No. 3, 2004, pp. 502-506.

Bar, Amir et al., "Evaluation of a Portable Device Based on Peripheral Arterial Tone for Unattended Home Sleep Studies", Chest, vol. 123, No. 3, Mar. 2003, pp. 695-703.

Morillo, D., Rojas Ojeda, J., Crespo Foix, L. and Jimenez, A., 2010. An Accelerometer-Based Device for Sleep Apnea Screening. IEEE Transactions on Information Technology in Biomedicine, 14(2), pp. 491-499. (Year: 2010).

European extended search report for EP Application No. 24180528. 2, mailed on Sep. 10, 2024, 7 pages.

Vlahandonis et al., Pulse transit time as a surrogate measure of changes in systolic arterial pressure in children during sleep, Journal of Sleep Research, vol. 23, 2014, pp. 406-413.

* cited by examiner

METHOD AND APPARATUS FOR NON-INVASIVE DETECTION OF PHYSIOLOGICAL AND PATHO-PHYSIOLOGICAL SLEEP CONDITIONS

RELATED APPLICATION

This application is a continuation application of U.S. application Ser. No. 16/207,520, filed Dec. 3, 2018, which is a continuation application of PCT Application No. PCT/M2017/053154, filed May 29, 2017, which relates to and claims priority to U.S. Provisional Application Ser. No. 62/347111, filed Jun. 8, 2016, the entirely of which is herein incorporated by reference.

FIELD OF INVENTION

The present invention and the present patent application relates to a method and apparatus for analyzing externally recorded physiological data of a patient for detecting and monitoring various breathing conditions of the patient.

In particular, this patent application relates to the analysis of circulatory pulse waveforms recorded from the body's surface of a patient, for determining changes in the performance of the heart during its contraction phase, due to the intra-thoracic pressure changes caused by the breathing cycle of the patient, and inferring there from the presence of certain breathing conditions and sleep disordered breathing conditions of the patient.

Further, the addition of external sensing means for determining respiratory activity, or for determining the pulse transmission time, (PTT), (also known as pulse transit time), or other physiological parameters may be beneficially used to enhance the characterization of sleep disordered breathing events, as will be explained in detail.

BACKGROUND AND PRIOR ART.

Several methods for using externally recorded blood pulse-waves to determine the nature of sleep related disordered breathing conditions have been previously described.

U.S. Pat. No. 5,385,144 "Respiration diagnosis apparatus, to Yamanishi et al, U.S. Pat. No. 6,856,829, "Method for detecting physiological condition of sleeping patient based on analysis of pulse" waves to Ohsaki et al and U.S. Pat. No. 6,669,632, "Apparatus and method for electronically predicting pleural pressure from pulse wave signals", to Nanba, Ohsaki, and Shiomi, are in general based on using the respiratory modulation patterns as indicators of pleural pressure fluctuations, which can be used to categorize apnea type.

These patents look at the envelope of series of pulsewaves to record the respiratory related changes. With greater pressure fluctuations in the chest during apneas, the level of the respiratory modulation increases, while the opposite applies in relation to central apnea.

In U.S. Pat. No. 5,385,144, characteristic patterns described by the time course of changes of the pulse signal baseline values (i.e. modulation patterns of the envelope of pulse signal baselines), are used to distinguish between central and obstructive sleep apneas, when the presence of sleep disordered breathing has initially been found on the basis of oximetry based oxygen desaturation events. The modulation patterns are considered both in terms of the magnitude or amplitude of the modulation, or to characteristic patterns of the shape of the modulation envelope.

U.S. Pat. No. 6,669,632, describes a method of determining pleural pressure based on determining the difference between a first envelope defined by connecting the peaks of consecutive pulse signals in a series of pulsewaves, (where the amplitude of the peaks of the pulses in the given time series of pulsewaves oscillates in time with the breathing cycle) as shown in FIG. 1A as "dashed" lines AA, and a second envelope defined by connecting consecutive peaks corresponding to the peaks of consecutive breathing cycles of the first envelope of pulsewaves, as also shown in FIG. 1A as "dotted" lines BB.

The difference between these two envelopes, represented by FIG. 1B, is said to correspond to the subject's pleural pressure over time. Alternatively, the heights of the pulse signal amplitudes, of some defined fraction of the amplitude can be used in the same process.

In U.S. Pat. No. 6,856,829, the patterns characterizing time-series of differences between individual pulsewave trough to peak signal amplitudes in a series of pulses are used to identify and categorize sleep related disordered breathing conditions. The time course of signal peaks, troughs, mid points, and trough to peak amplitudes envelopes (FIG. 2), reflect respiratory modulation, and this may be used to define presence or absence of apnea, and its type based on the size and frequency of amplitude fluctuations. Alternatively, the area under the curves of the pulse signals can be used instead of trough to peak differences.

While these kinds of analyses may be influenced by changes in intrathoracic pressure related to sleep related respiratory acts, there are some important limitations associated with these methods. One important consideration is that over time, normal physiological homeostatic regulation causes vascular tone to vary considerably and often inconsistently, which may modify the measured respiratory modulation amplitudes, and therefore adversely affect the accuracy of the above described analyses, and their interpretations as described in the above listed prior art patents. Similarly, the powerful vasomotor changes associated with arousals during sleep would greatly interfere with such analyses.

As will be explained in detail, the present invention overcomes these and other limitations which adversely affect accurate assessment of the physiological condition of the patient.

Additional Prior Art

In addition to the above described methods which are based on measuring peripheral pulses, other methods and apparatus for measuring respiratory activity and detecting and categorizing sleep disordered breathing conditions are known to the art. These include using apparatus applied to the body such as accelerometers, respiratory belts, impedance plethysmographic devices, sternal-notch movement sensors, and the like, for directly measuring respiratory activity. Such methods and apparatus require the application of sensing modalities to the patient, to facilitate the measurement of the breathing related conditions, and thus to help confirm the detection of disordered breathing events, and to help differentiate between the various types of these events.

For example, WO2011057116A, "Detection and differentiation of sleep disordered breathing", by Bauer P T. et al. describes a vector method using three-orthogonal-axis accelerometer(s) for monitoring a subject's sleep-disordered breathing and processing and analyzing collected data to detect associated, disordered breathing.

The inventors describe a preferred and best-mode manner of describing the their invention according to which; "it proposes a method for monitoring sleep-disordered breathing including the steps of (a) collecting, simultaneously, multi-facet, three-axis data from a sleeping subject utilizing an anatomy-attached, three-orthogonal-axis accelerometer, and (b) following such collecting, processing and analyzing the collected data to detect associated, disordered breathing including assessing the presence of at least one of (a) sleep-disordered breathing generally, (b) sleep apnea specifically, (c) differentiation between central and obstructive sleep apnea, and (d) hypopnea." According to these inventors "Preferably, the main signal-gathering device, the three-axis accelerometer, will be located on the subject's chest in a position on the thorax, such as the one mentioned above, so it can easily pick up respiratory movement."

U.S. Pat. No. 7,510,531. "System and method for discrimination of central and obstructive disordered breathing events", describes how disordered breathing events may be classified as central, obstructive or a combination of central an obstructive in origin based on patient motion associated with respiratory effort, wherein the components of the disordered breathing classification system may be fully or partially implantable, Similarly, the medical literature teaches methods and apparatus applied to the body for directly measuring respiratory activity for diagnosing sleep disordered breathing conditions, such as the paper by P. Dehkordi et al, who in their paper entitled "Monitoring torso acceleration for estimating the respiratory flow and efforts for sleep apnea detection". Conf Proc IEEE Eng Med Biol Soc 2012; 2012:6345-8, describe a method based on ensemble learning to estimate the respiratory flow, the thoracic respiratory effort and the abdominal respiratory effort from acceleration of suprasternal notch, the thorax and the abdomen respectively. The estimated flow can be used to detect the breathing cessations and the estimated efforts can be used to classify them into obstructive and central apneas. Results demonstrate the feasibility of using torso acceleration as a simple and inexpensive solution for long term measuring and monitoring of respiratory functions for sleep apnea detection.

A paper by Dillier R, et al; Continuous respiratory monitoring for sleep apnea screening by ambulatory hemodynamic monitor, World J Cardiol. 2012 Apr. 26; 4(4):121-7, describes the utilization of multiple lead ECG, heart sound signals, body position, snoring, and respiration. Body position and respiration are determined from a triaxial accelerometer. The data are downloaded to a PC application with automated algorithms for detection of respiration, including Sleep Disordered Breathing events, snoring, body position, and activity level. Differentiation between obstructive, central and mixed apneas were determined using conventional thermistors.

Morillo D S. et al. in their paper "Monitoring and analysis of cardio respiratory and snoring signals by using an accelerometer", Conf Proc IEEE Eng Med Biol Soc. 2007; 2007:3942-5, describe a system based on an accelerometer for acquisition and monitoring of diverse physiological signals, by extracting respiratory, cardiac and snoring components inside the main source. This allows the monitoring of several biomedical parameters: heart rate (HR), heart rate variability (HRV), Sympathetic, parasympathetic and baroreflex activity, respiratory rhythms and their variations (bradypnea-tachypnea), snoring and abdominal-thoracic efforts. A simple and effective method and device [1] is provided for helping to the diagnosis of Sleep Apnea-Hypopnea Syndrome (SAHS) and other breathing disorders.

Another paper by Morillo et al., "An accelerometer-based device for sleep apnea screening". IEEE Trans Inf Technol Biomed. 2010 Mar. 14 (2):491-9, describes a body-fixed-sensor-based approach to assess potential sleep apnea patients using an accelerator mounted on the suprasternal notch. Respiratory, cardiac, and snoring components were extracted by means of digital signal processing techniques. Results demonstrated the feasibility of implementing an accelerometry-based portable device as a simple and cost-effective solution for contributing to the screening of sleep apnea-hypopnea syndrome and other breathing disorders.

A landmark paper by Argod J, Pepin J L, Levy P, entitled "Differentiating obstructive and central sleep respiratory events through pulse transit time". Am J Respir Crit Care Med. 1998 December; 158 (6):1778-83, describes a noninvasive method for differentiating between obstructive and central sleep disordered breathing events based on the Pulse transit time (PTT), which is the time taken for pulse pressure to travel from the aortic valve to the periphery.

The authors demonstrated a close relationship between the increase in esophageal pressure (Pes), and a progressive rise in the amplitude of PTT oscillations, and showed that PTT has a high sensitivity and specificity in differentiating obstructive and central respiratory events.

While the above mentioned accelerometric based and PTT methods may be influenced by changes in intrathoracic pressure related to sleep related respiratory acts, there are some important limitations associated with these methods.

For example, accelerometric measurement is extremely sensitive to the degree of coupling to the body surface as well as to movement and posture changes of the patient which can adversely the accuracy of the assessments, and PTT measurement involves the use of multiple measurement modalities and requires a high degree of precision and complicated analysis for accurate assessments, as well as requiring careful instrumentation of the subject.

Thus, it can be seen that the various prior art methods described above, suffer from a variety of limitations of accuracy and ease of application and use.

As will be explained in detail, the present invention overcomes these and other limitations which adversely affect accurate assessment of the physiological condition of the patient.

In particular, the discrimination between obstructive sleep apnea, and central sleep apnea is a focal point of the present invention.

As is well known, obstructive sleep apnea, the more common form, is caused when upper airway partial or complete obstruction results in insufficient or absent ventilation, whereas central sleep apnea is caused by abnormal or periodically absent respiratory drive due to faulty central nervous system control of breathing.

This latter type of sleep apnea is far less common than obstructive sleep apnea and may well call for a far different treatment regimen.

Heretofore, it can be appreciated that there are a number of ways, given the above background information, by which sleep apnea events may be discovered, but not a simple methodology with which a discrimination can be made of obstructive versus central sleep apnea, which each have different causes and different modes of treatment. It is to this methodology that the present invention is directed.

SUMMARY OF THE PRESENT INVENTION

In an aspect, a method for the non-invasive detection of certain medical conditions and physiological states includes the steps of: monitoring circulatory pulse waveforms recorded from a person's body; monitoring circulatory pulse systolic upstroke waveforms recorded from a person's body; normalizing said circulatory pulse systolic upstroke waveforms such that the magnitude of the trough to peak amplitude of each such systolic upstroke is set to a predetermined value; determining at least one index of the upstroke to characterize the strength of the contraction of the heart during the systolic upstroke phase of a heart beat; determining changes of said at least one index of the upstroke to characterize the strength of the contraction of the heart during a series of heart beats related to a breathing cycle, or to an absent anticipated breathing cycle, of the patient; and, determining the certain medical conditions and physiological states based on changes of the at least one index of the upstroke related to a breathing cycle, or to an absent anticipated breathing cycle, of the patient.

In another aspect, the medical conditions and physiological states include one or more of: breathing conditions, certain sleep disordered breathing conditions, or assessment of the person's myocardial contractility, and its dynamic changes.

In a further aspect, said at least one index of the upstroke is determined utilizing any detected changes in said systolic upstroke, including one or more of: (a) changes in the dynamic signal time-course thereof, (b) the relative fraction of the entire systolic upstroke amplitude occurring within a prescribed period of time, (c) the relative fraction of the entire systolic upstroke amplitude occurring within a prescribed period of time commencing at a predetermined fraction of the entire systolic upstroke amplitude, (d) the time between predetermined fractions of the normalized upstroke, (e) as a rate of change moment of the systolic upstroke, or (f) as a moment of the systolic upstroke, and wherein the normalized systolic upstroke index is substantially unaffected by spontaneous changes in the pulse amplitude.

In yet another aspect, said breathing conditions, said certain sleep disordered breathing conditions, and said assessment of the myocardial contractility, and its dynamic changes, are determined by at least one of (a) analysis of time series patterns of derived upstroke index values; and, (b) sleep disordered breathing analysis based on monitoring at least circulatory pulse waveforms recorded from an person's body. Said monitoring circulatory pulse waveforms recorded from a person's body and said monitoring circulatory pulse systolic upstroke waveforms recorded from a person's body are made using one or more of: a peripheral arterial tone (PAT) measurement, volumetric change measurement, an optical density measurement, a surface-reflectivity measurement, a pulse oximetry measurement, an electrical resistivity measurement, a Doppler ultrasound measurement, a laser Doppler measurement, a flow meter device, a segmental plethysmograph, a circumferential strain gauge device, an optical plethysmograph, an optical plethysmograph signal derived from a pulse oximeter, an isotope washout device, a thermal washout device, a temperature measurement, a temperature change measurement, an electromagnetic measurement device, a sensor affected by a change in finger geometry or red blood cell alignment or flux associated with pulsatile volume changes, or Hall effect sensors.

In an aspect, said certain breathing conditions, certain sleep disordered breathing conditions, or assessment of the person's myocardial contractility, and its dynamic changes are selected from one or more of: sleep state, wake state, REM stage sleep, non-REM state sleep, non-REM light sleep state, non-REM deep sleep state, obstructive sleep apnea, central sleep apnea, mixed sleep apnea, obstructive sleep hypopnea, upper airway resistance syndrome, fixed or transient elevated respiratory resistance, respiratory effort related arousal (RERA), Chenye-Stokes breathing, Valsalva and Mueller maneuvers, or periodic limb movement syndrome.

In a further aspect, said sleep disordered breathing condition is one or more of: an obstructive, a central or of a mixed nature sleep disordered breathing condition based on the magnitude of change of the said analysis of a time series pattern of derived upstroke index values.

In yet a further aspect, said determination of certain breathing conditions, certain sleep disordered breathing conditions, or assessment of the person's myocardial contractility, and its dynamic changes are made by one or more measuring devices selected from: a peripheral arterial tone (PAT) signal, a pulsewave signal, pulse oximetry determined arterial blood oxygen saturation level (SaO2), a sleep wake detection method such as an actigraph device, an accelerometric signal measurement device, and at least one body position sensor and an acoustic sensor.

The method further includes the steps of: (a) detecting an accelerometric signal of the person, (b) analyzing the accelerometric signal, and (c) determining the person's certain breathing condition, or certain sleep disordered breathing condition based on one or more of: the upstroke changes analysis, the sleep disordered breathing analysis previously described in PAT technology related patents and patent applications and discussed in detail below, and the accelerometric signal analysis.

In another aspect, the assessment of the person's myocardial contractility is determined as one of: an absolute value of said upstroke index or a mean value of a series of upstroke index values, during at least one breathing cycle or an absent anticipated breathing cycle, and wherein the change over time of an absolute value of said upstroke index or a mean value of a series of upstroke index values during at least one breathing cycle or at least one absent anticipated breathing cycle, is a function of changes in a person's myocardial contractility over time.

In an aspect, a high level of variability in the time series of upstroke index during sleep indicates the presence of obstructive sleep apnea, and wherein a low level or no change in variability in the time series of upstroke index in the upstroke index during sleep indicates the presence of central sleep apnea and wherein a combination of high and low, or high and no variability, in the time series of upstroke index during sleep indicates the presence of mixed obstructive and central sleep apnea. The results of the diagnosis may be displayed by a display unit, as incorporated by reference from U.S. Pat. No. 6,856,829.

In another aspect, the incorporation of one or more of; accelerometric information, breathing sound information, pulse transit time (PTT) information, or factors which confirm a diagnosis based on the systolic upstroke analysis, and thereby to indicate the presence of an obstructive or central sleep apnea or a mixed obstructive and central sleep apnea event.

In another aspect, the high and low variability of the at least one upstroke index is determined based on comparison to the cyclic variability of upstroke index of a subject during: (a) at least one normal breathing cycle while asleep, (b) during at least one normal breathing cycle while awake, or (c) to a predefined threshold value. The determination of said sleep disordered breathing condition as being one of an obstructive, central or mixed nature based on the magnitude of change of the said analysis of a time series pattern of derived upstroke index values is further based on a pre-defined decline in blood oxygen saturation of the patient.

In an aspect, a system for the non-invasive detection of certain medical conditions and physiological states in a person includes a device that monitors circulatory pulse waveforms recorded from the person's body and monitors circulatory pulse systolic upstroke waveforms recorded from the person's body; the device normalizes said circu-latory pulse systolic upstroke waveforms such that the magnitude of the trough to peak amplitude of each such systolic upstroke is set to a predetermined value; determines at least one index of the upstroke to characterize the strength of the contraction of the heart during the systolic upstroke phase of a heart beat; determines changes of said at least one index of the upstroke during a series of heart beats wherein said at least one upstroke index is related to the breathing cycle or to an absent anticipated breathing cycle of the person; and, determines that the certain medical conditions and physiological states based upon the at least one index of the upstroke has been detected.

In another aspect, the medical conditions and physiologi-cal states include one or more of: breathing conditions, certain sleep disordered breathing conditions, or assessment of the person's myocardial contractility, and its dynamic changes.

The inventive method of the present invention is essen-tially based on measuring the effectiveness of the heart's pumping action, and in particular, to the influence exerted upon the heart's pumping action caused by intra thoracic pressure changes brought about by the patient's breathing cycle.

The interaction between the heart pumping action and the breathing cycle occurs in view of the heart's location in the thorax since it is situated in the midst of a constantly changing external pressure environment caused by the breathing cycle.

The pressure applied to the exposed heart may directly affect its pumping action in relation to the magnitude of the imposed pressure level; for example, increased negative intra-thoracic pressure would tend to oppose ventricular contraction, thereby reducing the effective rate blood ejec-tion from the ventricle. The effective influence of thoracic pressure fluctuations due to breathing on the pumping action of the heart may be conveniently determined non-invasively by measuring arterial pulsewave signals, and analyzing such signals to measure the effect on the contraction dynamics of the left ventricle to determine relative changes of the systolic upstroke (relative to the entire systolic upstroke).

This type of analysis may be performed in a host of ways, for instance by determining the fractional change in upstroke amplitude occurring within a prescribed period of time, from some prescribed fraction of the systolic upstroke, or by determining the time interval between prescribed fractions of the upstroke amplitude, to determine an upstroke index, and in many other ways.

While pulsewave detection is most readily and conve-niently performed using non-invasively recorded pulse wave forms from the body surface, it may also be applied to invasively determined arterial pulse waves.

As will be described, the method is of particular value in determining the acute influence of intra-thoracic pressure, and in particular short term changes of intra-thoracic pres-sure on the time-course of ejection of blood from the heart.

Information based on the dynamic changes of the sys-temic pulse-waves, which such intra-thoracic pressure changes produce, can be particularly helpful in recognizing certain types of naturally occurring respiratory acts, which may be associated with various physiological and patho-physiological states.

Specific examples of such respiratory events include: obstructive sleep apnea or hypopnea events, fixed or tran-sient elevated respiratory resistance, upper airways resis-tance, respiratory effort related arousals, central sleep apnea events, Valsalva and Mueller maneuvers, Chenye-Stokes breathing, and more.

Aside from detecting various breathing cycle related conditions, determining changes in the effectiveness of the heart's pumping action over time as reflected by the absolute value of an upstroke index, as well as its changes over time, may also provide a way of assessing myocardial contractil-ity, and its dynamic changes, without compromising the effectiveness of the respiratory event diagnosis.

The techniques described may be used in conjunction with any known method of measuring pulsewaves from the body, such as commonly available pulse oximeters, optical plethysmographs, pneumatic measurements methods such as those commonly used in blood pressure measurement devices, and many other methods, but may be of optimal value when used in combination with measurement methods for measuring the peripheral arterial tone (PAT), of patients, such as described in the following US patents and currently pending patents applications in the USA:

U.S. Pat. No. 6,319,205, Method And Apparatus For The Non-Invasive Detection Of Medical Conditions By Moni-toring Peripheral Arterial Tone, U.S. Pat. No. 6,461,305, Pressure Applicator Devices Particularly Useful For Non-Invasive Detection Of Medical Conditions, U.S. Pat. No. 6,916,289 Pressure Applicator Devices Particularly Useful For Non-Invasive Detection Of Medical Conditions, U.S. Pat. No. 6,488,633, Probe Devices Particularly Use-ful For Non-Invasive Detection Of Medical Conditions, U.S. Pat. No. 6,322,515, Method And Apparatus For The Non-Invasive Detection Of Medical Conditions By Moni-toring Peripheral Arterial Tone, U.S. Pat. No. 7,806,831, Method And Apparatus For The Non-Invasive Detection Of Particular Sleep-State Condi-tions By Monitoring The Peripheral Vascular System, U.S. Pat. No. 6,939,304, Method And Apparatus For Non-Invasively Evaluating Endothelial Activity In A Patient, U.S. Pat. No. 7,374,540, Non-Invasive Probe For Detect-ing Medical Conditions, U.S. Pat. No. 7,621,877, Body Surface Probe, Apparatus And Method For Non-Invasively Detecting Medical Con-ditions, U.S. Pat. No. 7,819,811, Detecting Medical Conditions With Noninvasive Body Probes, and corresponding foreign patents and patent applications, as well as the following pending applications in the USA and their respective corre-sponding foreign patents and patent applications;

PCT/IL/2011/662610, Non-invasively measuring physi-ological parameters, particularly blood flow and venous capacitance, PCT/IL2012/937737, Non-Invasive Apparatus And Method For Determining Sleep Stages, and PCT/IL2012/050466, Apparatus For Monitoring Arterial Pulse Waves In Diagnosing Various Medical Conditions, and PCT/IL2009/000528 Method And Apparatus For Exam-ining Subjects For Particular Physiological Conditions Uti-lizing Acoustic Information.

As mentioned, the method of the present invention may be used with particular benefit in conjunction with the above listed patents and patent applications, especially when these are directed to detecting the presence of sleep disordered breathing conditions, based on peripheral vascular changes.

PAT measurements, as discussed in the above listed patents and patent applications, confer substantial advantages in terms of the quality of the recorded pulse signal. Such advantages include the elimination of venous blood related pulse activity, the prevention of venous blood pooling (and thus induced veno-arteriolar reflex vasoconstriction) at the measurement site, optimization of the signal dynamic gain due to vascular wall tension reduction, etc.

In relation to the described prior art methods for using externally measured pulsewave signals for detecting breathing conditions, the present invention possesses a number of important advantages which are designed to avoid the substantial shortcomings of the prior art methods.

In particular, a major problem associated with these prior art methods is that normal circulatory system control involves a complex interaction of various homeostatic regulatory systems which affect the level of vascular tone, so that the ultimate level of pulse amplitude being measured is a result of the interaction of influences that can produce wide ranging and very large changes on the pulse amplitude, which could easily produce confounding results in the described prior art methods.

Such local vascular tone changes can result in very substantial degrees of vasoconstriction or vasodilation in the region of measurement. In fact, the potential degree of change in signal amplitude of, for example, the finger arterial bed, spans a one hundredfold range. This may be far greater than any systemic changes brought about by variations in the contraction of the heart. Thus, local vascular tone changes can greatly affect the signal amplitude, and may very well obscure pulse signal changes due to the heart's pumping action, and changes thereof, due to the intrathoracic pressure changes related to the sleep disordered breathing states.

Furthermore, as has been described in U.S. Pat. No. 6,319,205 to Goor et al, substantial local vascular tone changes (specifically, peripheral arterial tone changes), are associated with sleep apnea events and other sleep disordered breathing states, and the transition to normal breathing upon arousal, so that evaluation of sleep disordered breathing states based merely on pulse amplitude changes presumed to be related to thoracic pressure swings, is liable to be confounded by the local vascular changes.

In view of the prior art methods being primarily based on examining the time-course of the pulse signal's amplitude, it is to be appreciated that only in the presence of a stable level of systemic vascular tone can such analyses be expected to unambiguously reflect changes related to sleep related respiratory acts and breathing disorders. Such a stable level of vascular tone would be the exception rather than the rule.

In contrast, the method of the present invention is explicitly designed to avoid such confounding effects of vascular tone variations since:

(A) The upstroke index is based on information derived from normalized pulse amplitudes, and is therefore not affected by spontaneous changes in the pulse amplitude due to vasomotor tone variability, which may be very substantial, and similarly, is not susceptible to the well-known large amplitude changes in pulsewaves related to arousal during sleep, and, (B) the upstroke is inherently relatively stable in terms of its duration, and relatively little affected by heart rate changes, since it is the result of the hearts stereotypical pattern of electrical activation and conduction to the myocardial tissues. As such, the upstroke duration is a stable component of the cardiac cycle, further reducing the influence of vasomotor/arousal relate variability.

Thus, a major advantage of the currently described inventive method is that it facilitates quantification of the pulse signal changes due to the action of the heart as affected by the thoracic pressure, irrespective of vascular tone due to the contractile state musculature of the blood vessels themselves. This is a critical improvement over the prior art since, as mentioned, the above-mentioned vasomotor influences may be confounding, and thus obscure the true nature of the specific breathing related changes of interest.

DESCRIPTION OF THE PRESENT INVENTION AND ITS PREFERRED EMBODIMENTS

The present inventive method is essentially based on the steps of acquiring pulsatile arterial wave forms from the patient, transducing and digitizing signals, and, using a processor, conditioning the signal, determining the trough to peak of the systolic upstrokes of each such pulse, for example, based on identifying their respective turning points, calculating an upstroke index, and analyzing the pattern of changes of the upstroke index to determine the presence and nature of a particular breathing condition.

Figure 1A:
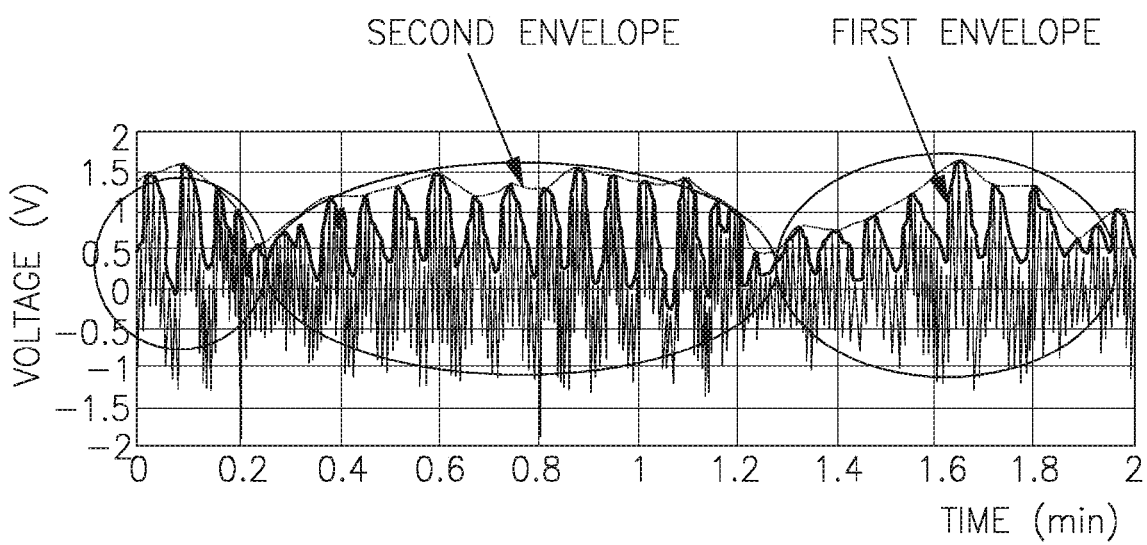
FIGS. 1A and 1B illustrate first and second envelopes of consecutive pulse signals and their difference between the two envelopes in a prior art method.
Figure 1B:
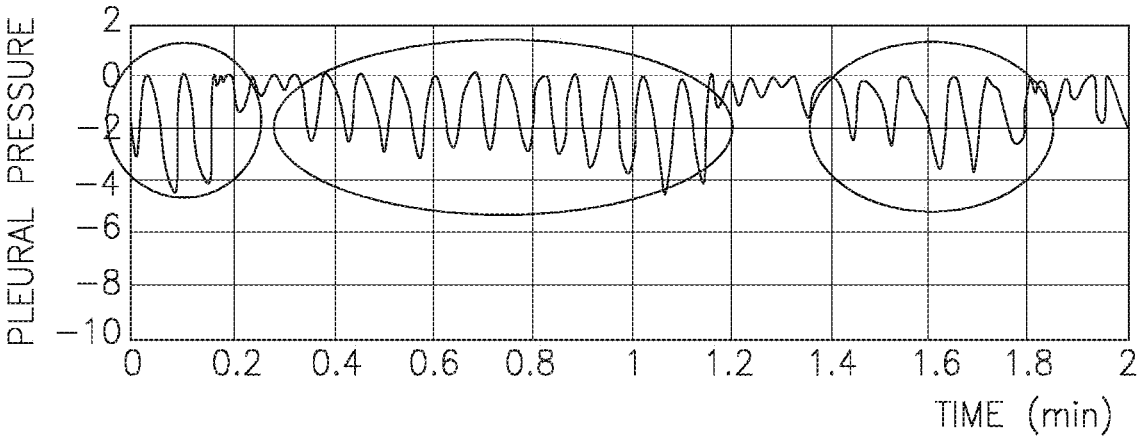
Figure 2:
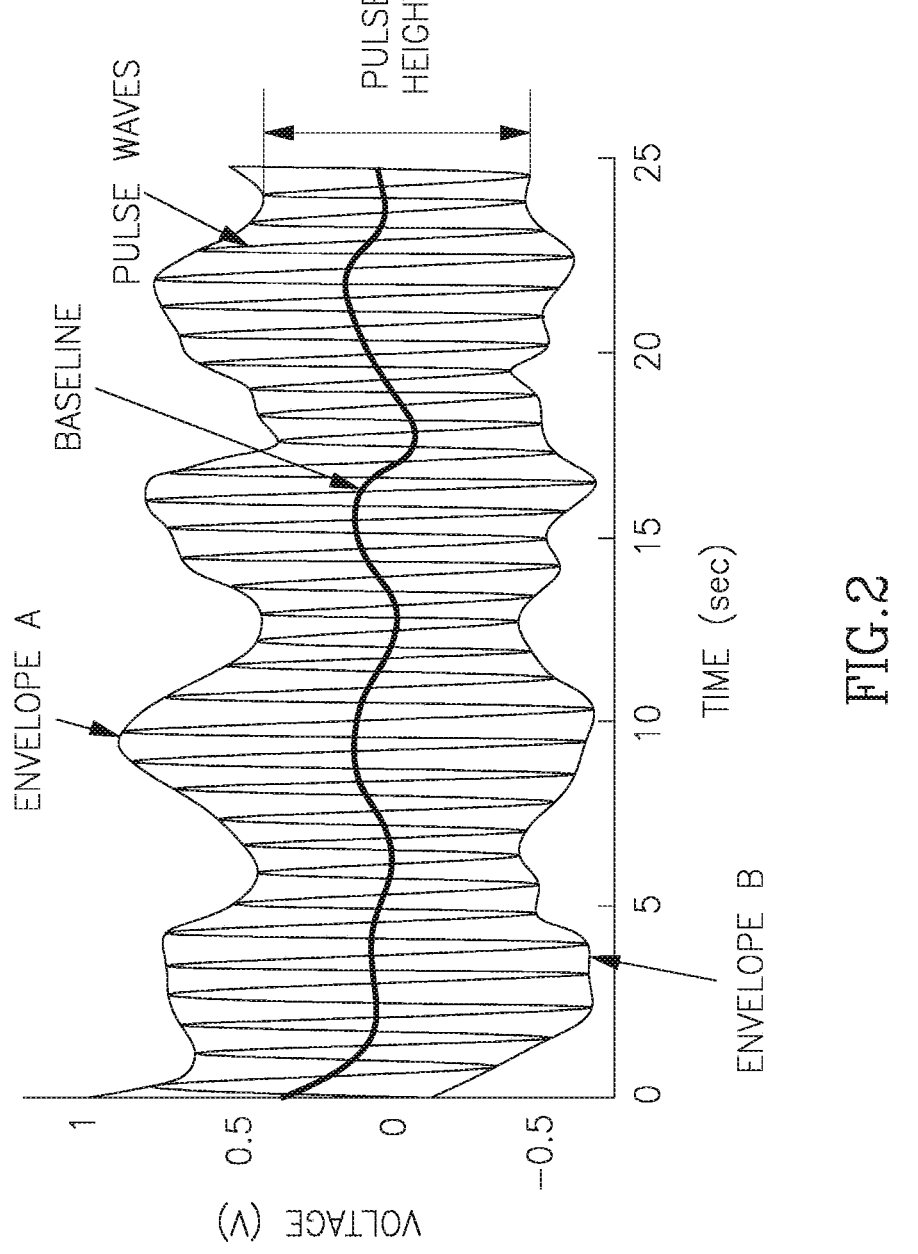
FIG. 2 illustrates pulsewave envelopes that reflect respiratory modulation in a prior art method.
Figures 3A, 3B:
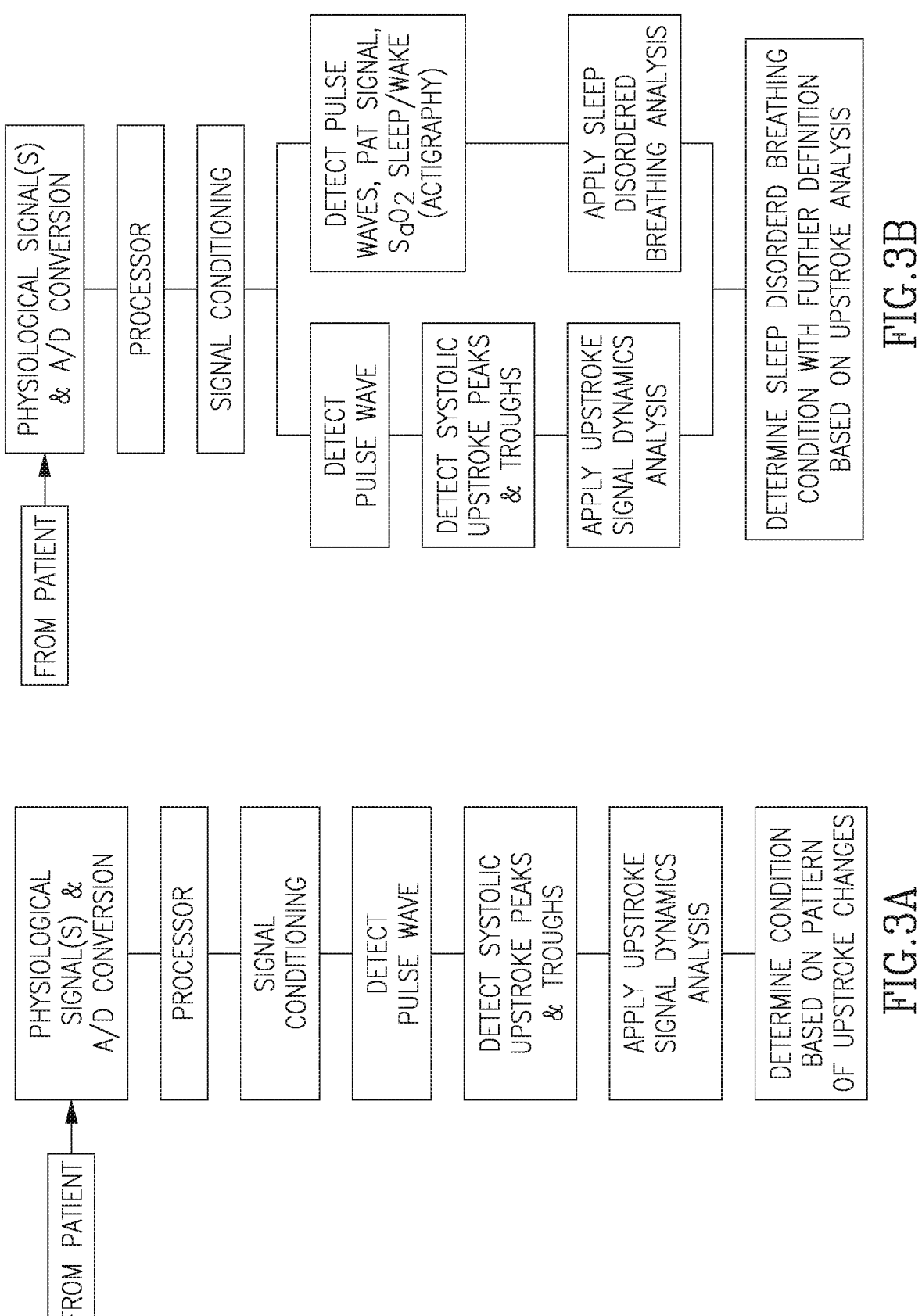
FIGS. 3A and 3B illustrate are flowcharts that illustrate applying an upstroke analysis to determine a breathing condition (A) and the same flowchart with the addition of a PAT signal or pulsewave and other signals, and sleep disordered breathing analysis, for detection of a sleep disordered breathing condition (B)

This sequence of steps is illustrated in FIG. 3A. As mentioned, this analysis is ideally used in combination with the peripheral arterial tone (PAT) signal, together with pulse oximetry determined arterial blood oxygen saturation level ($SaO_2$), (which may be derived from the same source as the PAT signal), and a sleep wake detection method such as an actigraph device, and sleep disordered breathing analysis, and their applications in the determination of various sleep related conditions as described in the above listed patents and patent applications. FIG. 3B schematically illustrates the nature of this combination.

Figure 4:
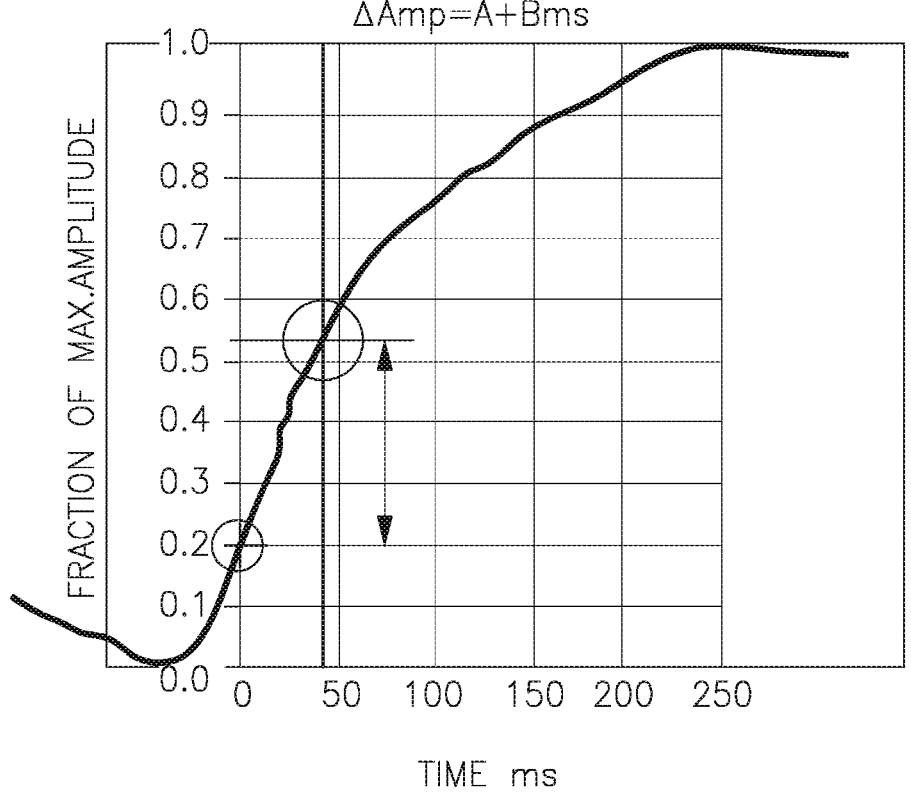
FIG. 4 illustrates an example of an approach to determining a normalized upstroke index.

FIG. 4 depicts an illustrative example of an approach to determining a normalized upstroke index based on the detection of the systolic upstroke peak and trough values. This, of course, may be determined in a great many ways, but for purposes of illustration only, this figure shows a method in which the fractional change in upstroke amplitude, (nominally depicted here as trough=0.00, and peak=1.00), is defined as the relative fraction of the upstroke occurring within a prescribed period of time of B milliseconds, from some prescribed fraction of the systolic upstroke (A), (such that the point of time at A can be more precisely determined than at a point nearer to the waveform trough or peak where the waveform is flatter). Many other ways of determining an upstroke index may be employed, using conventional analytical methods such as determining the time interval between prescribed fractions of the upstroke amplitude, etc.

Figure 5:
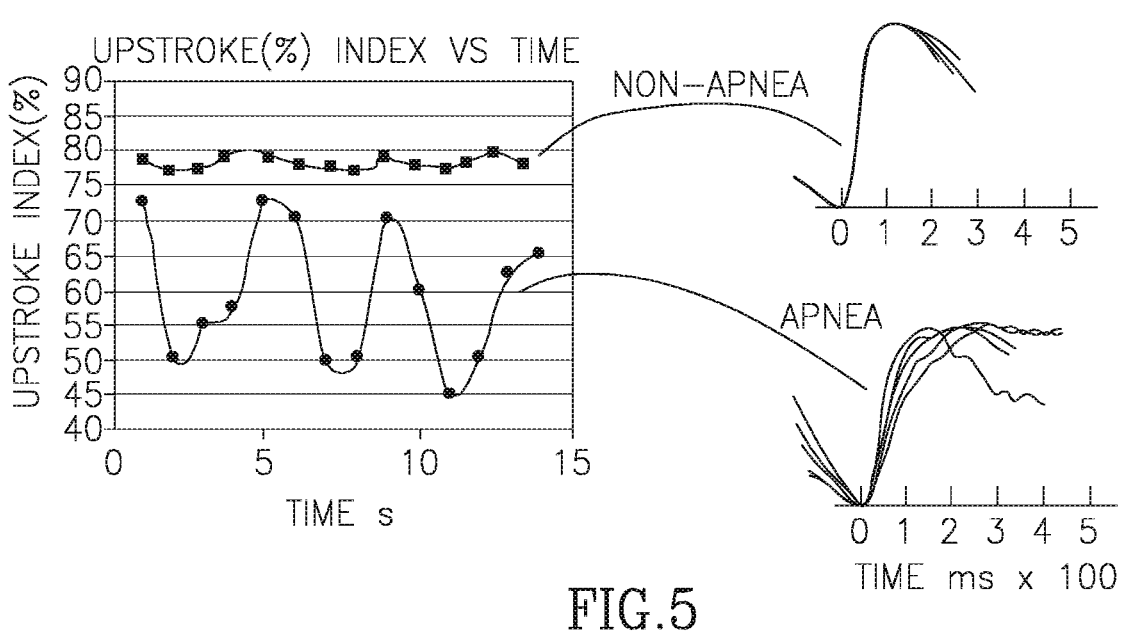
FIG. 5 illustrates contrasting patterns of 2-time series of upstroke indicia relating to an obstructive apnea (C) and non-apnea (B) conditions.

To illustrate the manner in which the time series patterns of derived upstroke index values can be used to assess particular breathing conditions, FIG. 5 shows the contrasting patterns of two series of such upstroke indices related to apnea and non-apnea states. The relative magnitude of the cyclic upstroke index changes in the apnea case are clearly much larger than for the non-apnea case, reflecting the greater fluctuations in intrathoracic pressure occurring during apneas due to greater fluctuations in respiratory effort during the course of a breathing cycle. The differences in the respective montages of serial upstrokes, normalized with respect to the trough to peak amplitude of each upstroke, and synchronized at the start of upstroke, is quite significant. The time courses of normalized upstrokes in the non-obstructed state (non-apnea), are remarkably consistent, in terms of low level of breathing cycle related variability of the upstroke index values, whereas the high level of breathing cycle related variability of the upstroke index values in the obstructed case (apnea) is clearly evident.

In the case of a central apnea event, in which even the normal respiratory effort associated with non-apneic breathing is absent, the magnitude of breathing cycle related variability of the upstroke index values would of course be less than during normal breathing, if not entirely absent. In the case of a combination of high and low or no variability in the time series of upstroke index during sleep indicates the presence of mixed obstructive and central sleep apnea.

Thus, the patient's individual level of breathing cycle related variability of the upstroke index values during non-apneic breathing may provide a functional threshold upon which to base the determination of a central apnea event, such that in the absence of breathing cycle related variability of the upstroke index values, or when such breathing cycle related pulse upstroke index variability is significantly less than during normal non-apneic breathing, absence of respiratory effort can be assumed to have occurred.

If this is associated with a progressive decline in blood oxygen saturation, then this would further confirm the diagnosis of a central apnea event.

Figure 6A:
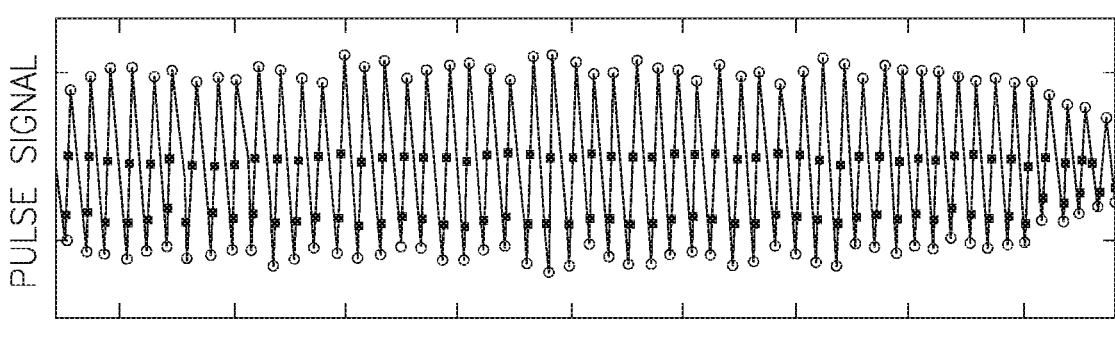
FIG. 6A illustrates the detailed time-course of a series of consecutive pulse signals (upper panel) and the corresponding upstroke index for each pulse signal (lower panel), and FIG. 6B showing similar pulse signals (upper panel) with noticeably different levels of upstroke index values (lower panel) in regions 1 and 2.
Figure 6A:
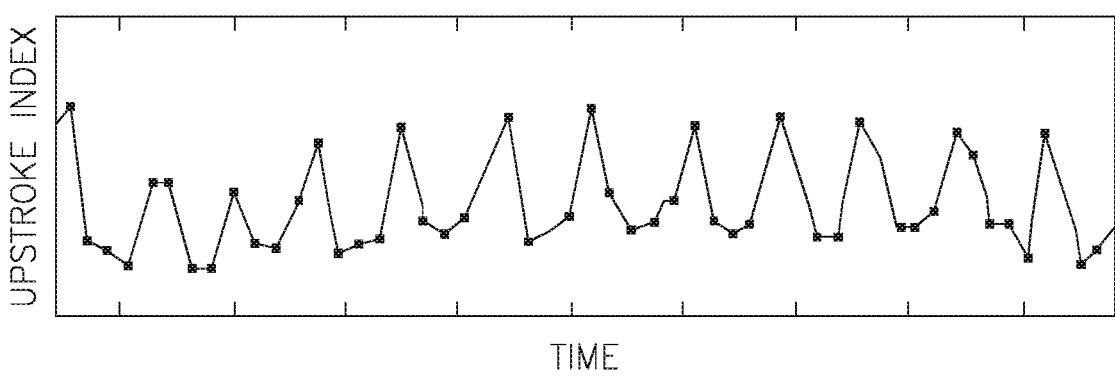

Similarly, if a period of below normal breathing cycle related variability of the upstroke index values is followed by an arousal as determined by patient movement, or by a vasoconstriction as detected by PAT or whatever pulse sensing modality is employed, or by an abrupt increase in blood oxygen saturation level (allowing for normal physiological lag time), then this too would further confirm the diagnosis of a central apnea event FIG. 6A illustrates the time-course of the upstroke index based on a series of consecutive pulse signals. In this example, the consistent pattern of breathing cycle related changes in the upstroke index can be clearly seen at 2, while the series of pulses appears to be of a generally consistent amplitude at 1.

Figures 6B, 7A, 7B:
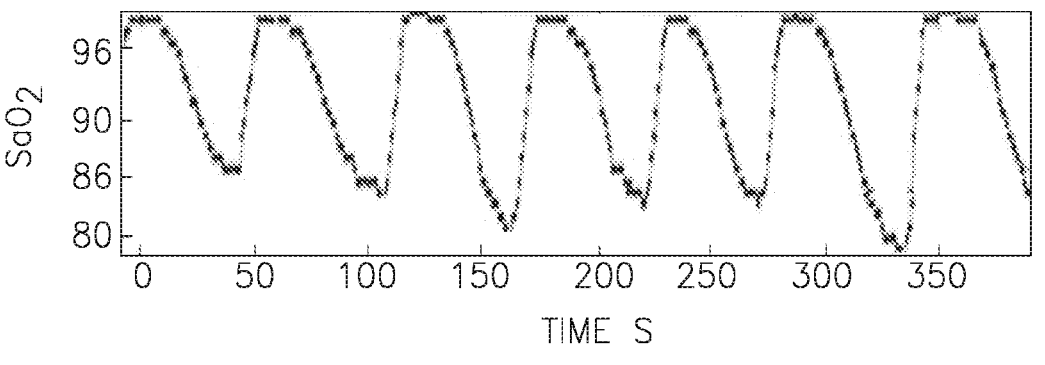
FIGS. 7A and 7B illustrate the time course of the upstroke index (A) and the corresponding blood oxygen saturation (B).

FIG. 6B shows examples of similar pulse wave signals associated with noticeably different levels of upstroke index. In the left of FIG. 6B at 1, it can be seen that the cyclic breathing related fluctuations of the upstroke index values are noticeably smaller than at 2, on the right side of FIG. 6B. Also, it can be seen that the pulsewave amplitudes in 1 and 2 are essentially the same, and importantly, no apparent differences can be discerned in the modulation of either series of pulsewaves. This helps to illustrate the advantage of the present method over the prior art.

In FIGS. 7A and 7B, the time course of the upstroke index (7A), and blood oxygen saturation (7B), are shown during a series of seven apneic events. The oximetry signal has been shifted to the left in order to compensate for the inherent lag of this parameter.

As can be seen, the magnitude of the fluctuations of each upstroke index appears to be increasing towards the end of each apnea. Interestingly, the upstroke signal appears to not be fluctuating in several time periods during these measurements. This is especially noticeable as from the onset of the third and fourth apneic events, where the upstroke signal is not fluctuating but is gradually declining over time, and in relation to the level of blood oxygen saturation.

This combination of declining saturation and non-fluctuating, or below normal breathing fluctuating levels of upstroke index is indicative of central sleep apnea, during which respiratory effort is absent or greatly diminished. Following such non-fluctuating upstroke index phase, there is an abrupt onset of large scale fluctuations of the upstroke index, characteristic of obstructive sleep apnea, which appears to be superimposed on a continuing decline in the absolute value of the index.

This pattern of central and then obstructive apnea is characteristic of the so called mixed apnea.

The progressive trend for the absolute value of the upstroke index to decline as the degree of saturation increases might also be useful to provide a relative index of declining myocardial contractility. This finding may have important clinical value in assessing the impact of blood oxygen desaturation on the heart.

In one specific embodiment of the present invention, the pulse waves to be used in the inventive method are derived from any pulse detection methods known to the art, and may be derived from any part of body from which a pulse signal can be measured. Detection modalities include, but are not limited to, optical plethymographic signals, which may be derived from a pulse oximeter or any other kind of photooptical signal device, and maybe obtained using either the known transmission or reflection modes, or any combination thereof, as well as any form of laser Doppler or Doppler system, volumetric plethysmographs, segmental plethysmographs, surface strain gauge and circumferential strain gauge devices, and any other devices which are affected by a change in the geometry of the body surface due to pulsewaves and blood volume changes, such as piezo and electromagnetic devices.

In another embodiment of the present invention, the pulse waves to be used in the inventive method are derived from any one of the peripheral arterial tone (PAT) measurement devises mentioned above, including, for example: U.S. Pat. Nos. 6,319,205, 6,461,305, 6,916,289, 6,488,633, 6,322, 515, 7,806,831, 6,939,304, 7,374,540, 7,621,877, 7,819,811, and corresponding foreign patents and patent applications, as well as the following currently pending applications in the USA and their respective corresponding foreign patents and patent applications; PCT/IL2012/937737, PCT/IL2012/050466, and PCT/IL/2011/662610.

As has been described at length in these patents and patent applications, the above PAT measurement devices confer substantial advantages to the measurement of the arterial pulse signals, including the prevention of blood pooling in the veins at the measuring site, the unloading of the tension in the arterial walls to promote optimal dynamic response of the signal, substantially prevent uncontrolled venous backflow at said measuring site, and prevent the occurrence of veno-arteriolar reflex vasoconstriction by preventing venous distension. The PAT probes may be applied to the digits of the hands or feet, or may be applied to any body surface region as described in U.S. Pat. No. 7,621,877 "Body Surface Probe, Apparatus And Method For Non-Invasively Detecting Medical Conditions".

Most importantly, in addition to determining the inventive systolic upstroke analysis of the present invention, according the above cited PAT related patents and patent applications, the same PAT signal information from which the systolic upstroke index is derived, may also be simultaneously used in the sleep disordered breathing analysis for the clinically validated detection of a host of sleep related physiological and pathophysiological states and conditions which include sleep/wake determination, sleep apnea events, sleep hypopnea events, upper airway resistance syndrome (UARS) events, Cheyne-Stokes breathing events, REM (rapid eye movements) sleep stage, periodic leg movement syndrome (PLMS) and arousals related to disordered breathing events during sleep, as described in the above cited patents and patent applications. This embodiment is schematically illustrated in FIG. 3B.

As described above, the addition of the present inventive method to the previously described PAT related broad diagnostic spectrum of sleep related disorders, may further enhance this diagnostic capability by facilitating the distinction between obstructive and central apneas, as well as providing a quantitative index of the degree of intra thoracic pressure changes associated with breathing, which may be of particular importance in the diagnosis and grading of subtle and hard to diagnose upper airway resistance syndrome (UARS) events. This may have far reaching clinical significance as it may provide a sensitive quantitative feedback index useful in optimizing the real time level of pressure application required by the patient from a therapeutic positive airway pressure (PAP) device.

In yet a further embodiment, the inventive method of the present application may be particularly beneficially used in conjunction with the method and apparatus described in PCT/IL2009/000528: "Method And Apparatus For Examining Subjects For Particular Physiological Conditions Utilizing Acoustic Information" since the apparatus used in that patent application includes both multi-axis accelerometric and sound recording apparatus which are coupled to the patient's torso.

Figures 8, 9:
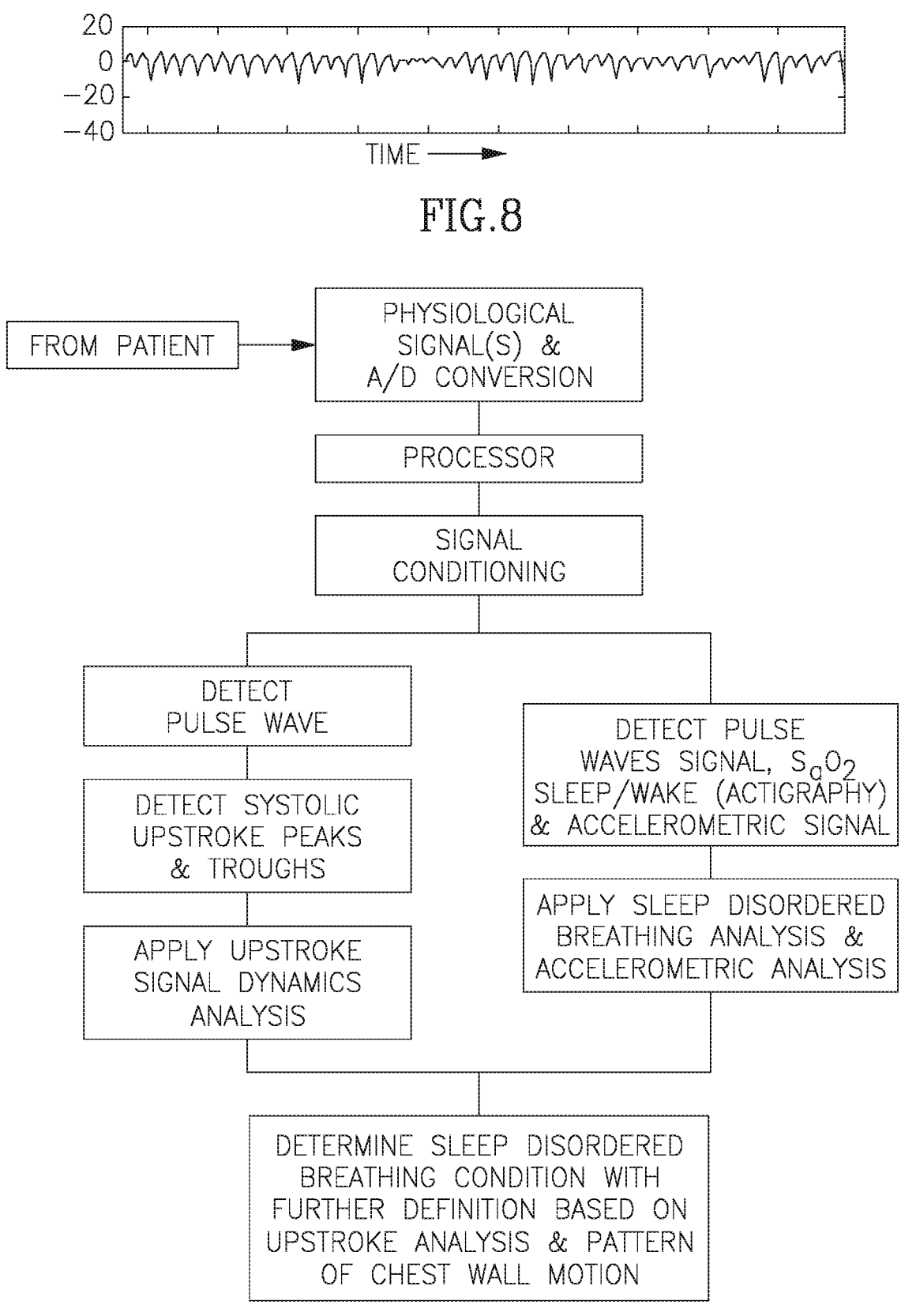
FIG. 8 illustrates a chart of an accelerometric output to provide a continuous signal reflecting the patient's breathing pattern.
FIG. 9 illustrates a flowchart of upstroke analysis with the PAT signal detected and breathing sound information.

As can be seen in FIG. 8, the accelerometric output can be used to provide a continuous signal which reflects the dynamic changes of the torso in relation to the patient's breathing.

When used in conjunction with PAT related evaluation of sleep disordered breathing events, this type of information allows the nature of the events to be more accurately determined. For instance, an apneic event which is not associated with accelerometric changes can be identified as a central apnea, as opposed to an obstructive apnea event, and vice versa. The actual clinical performance of the combination of PAT related evaluation of sleep disordered breathing, and added accelerometric information, has been found to accurately discriminate between obstructive and central apneas, with a sensitivity of 70.6%, and a specificity of 87.3%, relative to accepted clinical polysomnographic assessment. It is to be further noted that the analysis of such added chest wall motion information may be further improved with the addition of patient posture information, which may also be derived using multi-dimensional accelerometric data input, since the strength of the detected respiratory effort is affected by patient posture, for example, chest wall motion has weaker signal when the patient is in the prone position.

In addition, the quantitative assessment of respiratory related sounds, which as noted is a feature of PCT/IL2009/000528: "Method And Apparatus For Examining Subjects For Particular Physiological Conditions Utilizing Acoustic Information" may help to clarify the sleep disordered diagnosis, particularly in distinguishing between central and obstructive apneas, since the presence of respiratory related sound will rule out the diagnosis of central apnea.

A further way in which acoustic and/or accelerometric information can be used to differentiate between obstructive and central apneas, is related to their respective applications in the detection of cardiac cycle events, such as cardio-balistographic detection of ventricular contraction by accelerometry, and the acoustic detection of the heart sounds related to left ventricular systole, may be used in conjunction with the detection of peripheral pulsewaves to derive the PTT. As is well known, characteristic dynamic changes in PTT may be used to recognize obstructive apneas and thereby allow the distinction between central and obstructive events to be made. (See, Argod J, Pepin J L, Lévy P; "Differentiating obstructive and central sleep respiratory events through pulse transit time". Am J Respir Crit Care Med. 1998 December; 158(6):1778-83.).

Thus in this embodiment, the incorporation of the accelerometric information into the present inventive method as depicted in FIG. 9, with or without breathing sound information (not shown in FIG. 9), may thus help in confirming the diagnosis based on the systolic upstroke analysis, and furthermore, may be helpful in cases in which cardiac arrhythmias are present which may affect the frequency of pulse waves available for systolic upstroke analysis, or in cases where the pulse signal data is absent or otherwise compromised, such as during severe peripheral vasoconstriction.

While the above described embodiment of the present invention includes the use of an accelerometer applied to the patients torso and confers certain advantages as discussed above, the standalone embodiment of the invention without added apparatus applied to the torso as depicted in FIG. 3B has the important advantages of requiring minimal patient instrumentation, a reduced possibility of device failure, allows for maximal patient comfort and freedom of movement, and greatly simplifies the patient instrumentation, which is most important in a home based ambulatory test which is self-applied by the patient.

Figure 10:
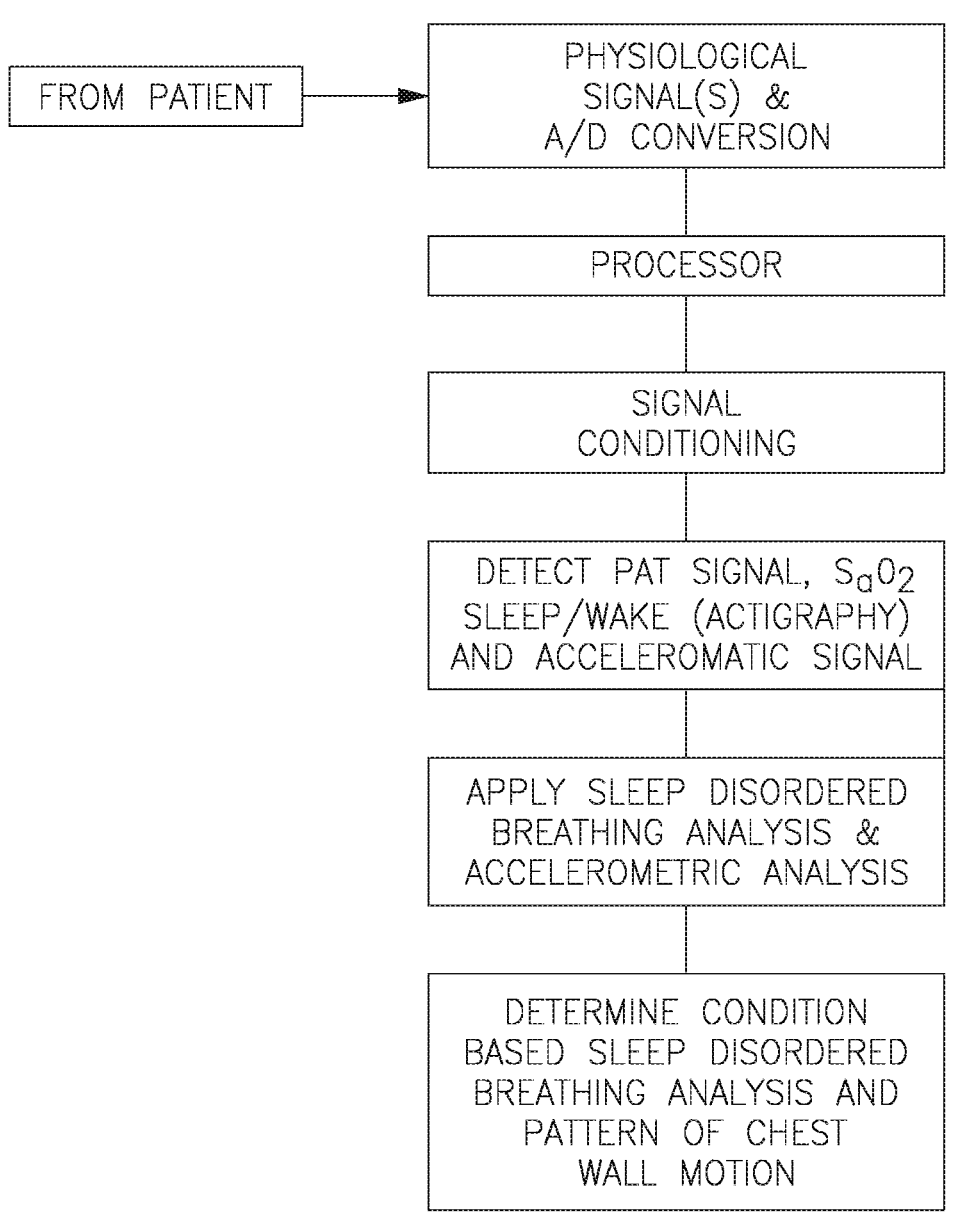
FIG. 10 illustrates a flowchart like that shown in FIG. 9 except without the upstroke analysis.

A further possible embodiment of the present invention is depicted in FIG. 10, which is essentially the same as that depicted in FIG. 9, but without analyzing the systolic upstroke.

The importance of this embodiment is that it provides a possible add-on means for distinguishing between central and obstructive sleep disordered events to an existing system in which pulse signals are not directly amenable for the described upstroke analysis. This might be helpful for example when the sampling rate of the pulsatile information is too low for accurately applying the upstroke analysis, or when the pulsatile information is presented as peak to trough amplitude differences only.

It may also be applicable as a backup for the embodiment illustrated in FIG. 9, in the event that the pulsewave signal is temporarily unavailable, for example, when blood flow to the measurement site is absent or diminished due to occlusion during a blood pressure measurement, or due to physiologically mediated vasoconstriction, or due to failure of the signal.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

I claim:

1. A system configured for non-invasive distinction between obstructive and central apnea conditions comprising:

a display unit, a patient sensor configured to be disposed on a body of a patient, wherein the patient sensor is configured to monitor a physiological signal of the patient, and a processor in communication with the patient sensor and the display unit, the processor configured to:

receive, from the patient sensor, the physiological signal of the patient, determine circulatory pulse systolic upstroke waveforms based on the physiological signal of the patient as a time series of systolic upstroke values, wherein each systolic upstroke value corresponds to a systolic upstroke phase of a heartbeat of a patient, normalize the systolic upstroke values to provide normalized systolic upstroke values by setting a magnitude of a trough to peak amplitude of each systolic upstroke value to a predetermined magnitude value, wherein the normalized systolic upstroke values are substantially unaffected by vascular tone due to the contractile state of the musculature of the blood vessels of the patient;

determine a variability of the normalized systolic upstroke values, wherein the variability of the normalized systolic upstroke values represent a change in strength of contractions of a heart as affected by intra-thoracic pressure related to breathing;

analyze the variability of the normalized systolic upstroke values;

determine, based on analyzing the variability of the normalized systolic upstroke values, presence of a central sleep apnea condition, an obstructive sleep apnea condition, or a mixed obstructive and central sleep apnea condition by:

determining the presence of the central sleep apnea condition upon a determination of a low level or no change in the variability of the normalized systolic upstroke values;

determining the presence of the obstructive sleep apnea condition upon a determination of a high level of variability of the normalized systolic upstroke values; and determining the presence of the mixed obstructive sleep and central sleep apnea condition upon a determination of a combination of high and low, or high and no variability, of variability of the normalized systolic upstroke values; and provide, via the display unit, an indication of the presence of the central sleep apnea condition, the obstructive sleep apnea condition, or the mixed obstructive and central sleep apnea condition.

2. The system of claim 1, wherein setting the predetermined magnitude value eliminates the contractile state of the blood vessels of the patient effects on the circulatory pulse systolic upstroke waveforms.

3. The system of claim 1, wherein the processor is further configured to:

analyze the variability of the normalized systolic upstroke values based on comparing the variability to one or more of cyclic variability of the normalized systolic upstroke values of the patient during: (a) at least one normal breathing cycle while asleep, (b) during at least one normal breathing cycle while awake, or (c) to a predefined threshold value.

4. The system of claim 3, wherein the processor is further configured to:

determine the presence of the central sleep apnea condition, the obstructive sleep apnea condition, or the mixed obstructive and central sleep apnea condition based on at least a magnitude of change of an analysis of the time series of the normalized systolic upstroke values.

5. The system of claim 4, wherein the processor is further configured to:

determine the presence of the central sleep apnea condition, the obstructive sleep apnea condition, or the mixed obstructive and central sleep apnea condition based on at least the magnitude of change of the analysis of the time series of the normalized systolic upstroke values and a predefined decline in blood oxygen saturation of the patient.

6. The system of claim 1, wherein the processor is further configured to:

analyze the variability of the normalized systolic upstroke values based on a predetermined functional threshold, wherein the functional threshold is based on determining if breathing cycle variability is less than during normal non-apneic breathing.

7. The system of claim 1, wherein the processor is further configured to:

analyze the variability of the normalized systolic upstroke values to determine a functional threshold for a high level of variability;

analyze the variability of the normalized systolic upstroke values to determine a functional threshold for a low level of variability;

determine, based on the respective high or low functional thresholds, an indication of a type of sleep apnea condition;

identify, the type of sleep apnea condition, wherein a value of the variability of the normalized systolic upstroke values above the functional high threshold comprises a high level of variability that indicates the presence of obstructive sleep apnea conditions, identify, the type of sleep apnea condition, wherein the value below the functional threshold comprises a low level of variability that indicates the presence of central sleep apnea, and identify, the type of sleep apnea condition, wherein values which are alternatively above the functional high threshold of a variability that indicates the presence of obstructive apnea conditions and below the functional low threshold of a variability that indicates the presence of central apnea, indicates the presence of mixed sleep apnea.

8. The system of claim 1, wherein the processor is further configured to:

further determine a decline in blood oxygen saturation of the patient, and analyze the variability of the normalized systolic upstroke values along with the decline in the blood oxygen saturation of the patient to determine one or more of the presence of the central sleep apnea condition, the obstructive sleep apnea condition, or the mixed obstructive and central sleep apnea condition.

9. The system of claim 1, wherein the patient sensor comprises a finger sensor configured to sense the physiological signal based on a finger arterial bed.

10. The system of claim 1, wherein the patient sensor comprises a sensor disposed on any part of body from which a pulse signal can be measured and is configured to sense the physiological signal based on an arterial bed.

11. The system of claim 1, wherein the processor is configured to provide the normalized systolic upstroke value based on a change over a predetermined period of time in amplitude value of a fraction of an overall amplitude value of the normalized systolic upstroke value, or a change of time over a predetermined range of fractions of an overall amplitude value of the normalized systolic upstroke.

12. The system of claim 1, wherein the processor is configured to determine the high level and the low level of the variability of the normalized systolic upstroke values based on comparison to a monitored physiological signal based on at least one breathing cycle of the body of the patient while the patient is awake.

13. The system of claim 12, wherein the variability of the normalized systolic upstroke values is determined utilizing a time between predetermined fractions of at least one index of a normalized upstroke.

14. The system of claim 1, further comprising one or more of a pulse oximeter a laser Doppler system, a volumetric plethysmographs, a segmental plethysmographs, a surface strain gauge, a circumferential strain gauge device, a piezoelectric device, and/or an electromagnetic device.

*    *    *    *    *